(12) United States Patent
Kim et al.

(10) Patent No.: US 10,655,118 B2
(45) Date of Patent: May 19, 2020

(54) HEAT-RESISTANT AGARASE AND MONOSACCHARIDE PRODUCTION METHOD USING SAME

(71) Applicant: Korea University Research and Business Foundation, Seoul (KR)

(72) Inventors: Kyoung Heon Kim, Seoul (KR); In-Geol Choi, Seoul (KR); Jung Hyun Kim, Seoul (KR); Eun-Ju Yun, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 71 days.

(21) Appl. No.: 16/067,730

(22) PCT Filed: Jan. 17, 2017

(86) PCT No.: PCT/KR2017/000561
§ 371 (c)(1),
(2) Date: Jul. 2, 2018

(87) PCT Pub. No.: WO2017/126862
PCT Pub. Date: Jul. 27, 2017

(65) Prior Publication Data
US 2019/0024069 A1 Jan. 24, 2019

(30) Foreign Application Priority Data
Jan. 19, 2016 (KR) .................. 10-2016-0006589

(51) Int. Cl.
*C12P 19/14* (2006.01)
*C12N 9/38* (2006.01)
*C12P 19/02* (2006.01)

(52) U.S. Cl.
CPC ............ *C12N 9/2468* (2013.01); *C12P 19/02* (2013.01); *C12P 19/14* (2013.01); *C12Y 302/01081* (2013.01)

(58) Field of Classification Search
CPC ............................................. C12Y 302/01081
See application file for complete search history.

(56) References Cited

U.S. PATENT DOCUMENTS

| 8,795,989 B2 * | 8/2014 | Hutcheson ............. | C12N 11/02 435/100 |
| 9,297,000 B2 * | 3/2016 | Choi ....................... | C12P 19/14 |
| 9,902,983 B2 * | 2/2018 | Kim ........................ | C12P 19/02 |
| 2015/0216778 A1 | 8/2015 | Kim et al. | |
| 2016/0279156 A1 | 9/2016 | Kang et al. | |

FOREIGN PATENT DOCUMENTS

| KR | 10-2010-0040438 A | 4/2010 |
| KR | 10-2013-0085017 A | 7/2013 |
| KR | 10-1489732 B1 | 2/2015 |

OTHER PUBLICATIONS

NCBI, agarase [Saccharophagus degradans], NCBI Reference Sequence: WP_011467657.1, Jul. 11, 2013, 3 pages.
NCBI, Saccharophagus degradans 2-40, complete genome, GenBank: CP000282.1, Feb. 10, 2014, 55 pages.
Hee Taek Kim et al., "The complete enzymatic saccharification of agarose and its application to simultaneous saccharification and fermentation of agarose for ethanol production," Bioresource Technology, 2012, pp. 301-306, vol. 107.
Hee Taek Kim et al., "High temperature and low acid pretreatment and agarase treatment of agarose for the production of sugar and ethanol from red seaweed biomass," Bioresource Technology, 2013, pp. 582-587, vol. 136.
Chan Hyoung Lee et al., "A Novel Agarolytic β-Galactosidase Acts on Agarooligosaccharides for Complete Hydrolysis of Agarose into Monomers," Applied and Environmental Microbiology, Oct. 2014, pp. 5965-5973, vol. 80, No. 19.
Chan Hyoung Lee et al., "Saccharification of agar using hydrothermal pretreatment and enzymes supplemented with agarolytic β-galactosidase," Process Biochemistry, 2015, pp. 1629-1633, vol. 50.
Fu et al., "Gene Cloning, Expression, and Characterization of a β-Agarase, AgaB34, from Agarivorans albus YKW-34," Journal of Microbiology and Biotechnology, 2009, pp. 257-264, vol. 19, No. 3.
Uyangaa Temuujin et al., "Overexpression and biochemical characterization of DagA from Streptomyces coelicolor A3(2): an endo-type β-agarase producing neoagarotetraose and neoagarohexaose," Appl Microbiol Biotechnol, Jun. 8, 2011, pp. 749-759, vol. 92.
Y. Ohta et al., "Enzymatic properties and nucleotide and amino acid sequences of a thermostable β-agarase from a novel species of deep-sea Microbulbifer," Appl Microbiol Biotechnol, Feb. 20, 2004, pp. 505-514, vol. 64.
International Searching Authority, International Search Report of PCT/KR2017/000561 dated Apr. 18, 2017.

* cited by examiner

Primary Examiner — Tekchand Saidha
(74) Attorney, Agent, or Firm — Sughrue Mion, PLLC

(57) ABSTRACT

The present invention relates to a heat-resistant agarase and a monosaccharide production method using same. More particularly, in the present invention, a heat-resistant agarase may be used to produce galactose and 3,6-anhydro-L-galactose at high yield by efficiently breaking down agarose or agar without a chemical pretreatment, a neutralization process, or an agarotriose hydrolase treatment process.

3 Claims, 13 Drawing Sheets
Specification includes a Sequence Listing.

SEQUENCE LISTING

<160> NUMBER OF SEQ ID NOS: 6

<210> SEQ ID NO 1
<211> LENGTH: 598
<212> TYPE: PRT
<213> ORGANISM: Saccharophagus degradans 2-40

<400> SEQUENCE: 1

Met Lys Thr Thr Lys Cys Ala Leu Ala Ala Leu Phe Phe Ser Thr Pro
1               5                   10                  15

Leu Met Ala Ala Asp Trp Asp Gly Ile Pro Val Pro Ala Asp Pro Gly
            20                  25                  30

Asn Gly Asn Thr Trp Glu Leu Gln Ser Leu Ser Asp Asp Phe Asn Tyr
        35                  40                  45

Ala Ala Pro Ala Asn Gly Lys Ser Thr Thr Phe Tyr Ser Arg Trp Ser
    50                  55                  60

Glu Gly Phe Ile Asn Ala Trp Leu Gly Pro Gly Gln Thr Glu Phe Tyr
65                  70                  75                  80

Gly Pro Asn Ala Ser Val Glu Gly Gly His Leu Ile Ile Lys Ala Thr
                85                  90                  95

Arg Lys Pro Gly Thr Thr Gln Ile Tyr Thr Gly Ala Ile His Ser Asn
            100                 105                 110

Glu Ser Phe Thr Tyr Pro Leu Tyr Leu Glu Ala Arg Thr Lys Ile Thr
        115                 120                 125

Asn Leu Thr Leu Ala Asn Ala Phe Trp Leu Leu Ser Ser Asp Ser Thr
    130                 135                 140

Glu Glu Ile Asp Val Leu Glu Ser Tyr Gly Ser Asp Arg Ala Thr Glu
145                 150                 155                 160

Thr Trp Phe Asp Glu Arg Leu His Leu Ser His His Val Phe Ile Arg
                165                 170                 175

Gln Pro Phe Gln Asp Tyr Gln Pro Lys Asp Ala Gly Ser Trp Tyr Pro
            180                 185                 190

Asn Pro Asp Gly Gly Thr Trp Arg Asp Gln Phe Phe Arg Ile Gly Val
        195                 200                 205

Tyr Trp Ile Asp Pro Trp Thr Leu Glu Tyr Tyr Val Asn Gly Glu Leu
    210                 215                 220

-continued

Val Arg Thr Val Ser Gly Pro Glu Met Ile Asp Pro Tyr Gly Tyr Thr
225                 230                 235                 240

Asn Gly Thr Gly Leu Ser Lys Pro Met Gln Val Ile Phe Asp Ala Glu
            245                 250                 255

His Gln Pro Trp Arg Asp Glu Gln Gly Thr Ala Pro Pro Thr Asp Ala
        260                 265                 270

Glu Leu Ala Asp Ser Ser Arg Asn Gln Phe Leu Ile Asp Trp Val Arg
    275                 280                 285

Phe Tyr Lys Pro Val Ala Ser Asn Asn Gly Gly Asp Pro Gly Asn
290                 295                 300

Gly Gly Thr Pro Gly Asn Gly Gly Ser Gly Asp Thr Val Val Glu
305                 310                 315                 320

Met Ala Asn Phe Ser Ala Thr Gly Lys Glu Gly Ser Ala Val Ala Gly
                325                 330                 335

Asp Thr Phe Thr Gly Phe Asn Pro Ser Gly Ala Asn Asn Ile Asn Tyr
            340                 345                 350

Asn Thr Leu Gly Asp Trp Ala Asp Tyr Thr Val Asn Phe Pro Ala Ala
        355                 360                 365

Gly Asn Tyr Thr Val Asn Leu Ile Ala Ala Ser Pro Val Thr Ser Gly
370                 375                 380

Leu Gly Ala Asp Ile Leu Val Asp Ser Ser Tyr Ala Gly Thr Ile Pro
385                 390                 395                 400

Val Ser Ser Thr Gly Ala Trp Glu Ile Tyr Asn Thr Phe Ser Leu Pro
                405                 410                 415

Ser Ser Ile Tyr Ile Ala Ser Ala Gly Asn His Thr Ile Arg Val Gln
            420                 425                 430

Ser Ser Gly Gly Ser Ala Trp Gln Trp Asn Gly Asp Glu Leu Arg Phe
        435                 440                 445

Thr Gln Thr Asp Ala Asp Thr Gly Thr Asn Pro Pro Ser Thr Ala Ser
    450                 455                 460

Ile Ala Val Glu Ala Glu Asn Phe Asn Ala Val Gly Thr Phe Ser
465                 470                 475                 480

Asp Gly Gln Ala Gln Pro Val Ser Val Tyr Thr Val Asn Gly Asn Thr
                485                 490                 495

Ala Ile Asn Tyr Val Asn Gln Gly Asp Tyr Ala Asp Tyr Thr Ile Ala
            500                 505                 510

Val Ala Gln Ala Gly Asn Tyr Thr Ile Ser Tyr Gln Ala Gly Ser Gly
        515                 520                 525

Val Thr Gly Gly Ser Ile Glu Phe Leu Val Asn Glu Asn Gly Ser Trp
    530                 535                 540

Ala Ser Lys Thr Val Thr Ala Val Pro Asn Gln Gly Trp Asp Asn Phe
545                 550                 555                 560

Gln Pro Leu Asn Gly Gly Ser Val Tyr Leu Ser Ala Gly Thr His Gln
                565                 570                 575

Val Arg Leu His Gly Ala Gly Ser Asn Asn Trp Gln Trp Asn Leu Asp
            580                 585                 590

Lys Phe Thr Leu Ser Asn
        595

<210> SEQ ID NO 2
<211> LENGTH: 1797
<212> TYPE: DNA
<213> ORGANISM: Saccharophagus degradans 2-40

<400> SEQUENCE: 2

```
atgaaaacca ccaaatgcgc cctagctgcg ctcttcttca gtacccctct tatggctgca      60
gattgggacg gaattcctgt cccagcggac ccagggaatg caacacctg ggagctacag      120
tccctttctg acgatttcaa ctatgcggcc ccagctaacg gcaaaagcac caccttctat     180
agccgctgga gcgaaggctt tatcaatgct tggctcggcc cggggcaaac cgagttttac     240
ggccccaatg cttcggtaga aggcggccac cttattatta aggccactcg caagccaggt     300
actactcaaa tttacactgg agcaattcac tccaatgaaa gttttaccta cccattgtat     360
ttggaagcgc gcaccaaaat tacaaacctc accctcgcca acgcattttg gctactaagc     420
tcagattcca ccgaagagat tgatgtgctg gagtcttacg gcagcgaccg tgcaacagaa     480
acgtggtttg acgaacgcct acacttaagc catcacgttt ttatccgcca gccatttcaa     540
gactaccaac cgaaagatgc aggcagctgg taccccaacc ccgatggcgg cacttggcgc     600
gaccaatttt tccgtatagg tgtttattgg atagaccccat ggacactgga gtattacgtg     660
aatggcgaat tagtgcgcac tgtaagcggc cagaaatga ttgacccgta cggttacacc      720
aacggcacag gcctaagtaa acccatgcaa gttatttcg atgcagagca tcagccttgg      780
cgcgacgaac aaggtactgc cccacccacc gacgcagagc tagccgactc gagtcgcaat     840
caattcttaa ttgactgggt gcgattctac aaacccgtgg caagcaacaa tggtggcggc     900
gacccaggca atggcggcac cccaggtaat ggtggcagtg gcgatactgt agtggtagaa     960
atggccaact ctctgccac aggtaaagaa ggctctgcag ttgcaggcga cactttcaca    1020
ggcttcaacc ccagcggcgc gaacaacatc aactacaaca ccttagggga ttgggcagac     1080
tacacggtga acttccccgc tgccggtaat tacaccgtaa acctaattgc agcctcgccg     1140
gttacatctg gctgggtgc agatattttg gtagacagca gttacgcagg caccatacct     1200
gttagcagca ccggagcttg ggagatatac aacacccttta gcttgcccag ctcgatttat     1260
atcgcaagcg caggcaatca tactattcgc gtacaaagct ccggcggtag cgcttggcag     1320
tggaacggcg acgaacttcg ctttacccaa acggatgcgg atacaggcac caatccaccc     1380
agtacagcca gcatagcggt tgaagccgaa aactttaacg cggtgggcgg caccctttagc    1440
gatggtcaag ctcaacctgt tagcgtttac accgttaacg caacactgc cattaactac     1500
gtaaaccaag gcgattatgc cgactacacc attgctgttg cccaagcggg taactacacc     1560
attagctatc aagctggcag tggcgtaaca ggtggtagca tagagttttt ggttaacgaa     1620
aacggaagct gggccagtaa aaccgttacc gccgtaccaa accaaggttg ggataacttc    1680
caacccttaa acgaggcag cgtttaccta agccaggca cccaccaagt tcgtttacac       1740
ggcgctggca gcaacaactg gcagtggaac ctagataagt tcacgcttag caactaa       1797
```

<210> SEQ ID NO 3
<211> LENGTH: 747
<212> TYPE: PRT
<213> ORGANISM: Saccharophagus degradans 2-40

<400> SEQUENCE: 3

Met Leu Phe Asp Phe Glu Asn Asp Gln Val Pro Ser Asn Ile His Phe
1               5                   10                  15

Leu Asn Ala Arg Ala Ser Ile Glu Thr Tyr Thr Gly Ile Asn Gly Glu
            20                  25                  30

Pro Ser Lys Gly Leu Lys Leu Ala Met Gln Ser Lys Gln His Ser Tyr
        35                  40                  45

Thr Gly Leu Ala Ile Val Pro Glu Gln Pro Trp Asp Trp Ser Glu Phe

```
            50                  55                  60
Thr Ser Ala Ser Leu Tyr Phe Asp Ile Val Ser Val Gly Asp His Ser
 65                  70                  75                  80

Thr Gln Phe Tyr Leu Asp Val Thr Asp Gln Asn Gly Ala Val Phe Thr
                 85                  90                  95

Arg Ser Ile Asp Ile Pro Val Gly Lys Met Gln Ser Tyr Tyr Ala Lys
            100                 105                 110

Leu Ser Gly His Asp Leu Glu Val Pro Asp Ser Gly Asp Val Asn Asp
            115                 120                 125

Leu Asn Leu Ala Ser Gly Leu Arg Ser Asn Pro Pro Thr Trp Thr Ser
130                 135                 140

Asp Asp Arg Gln Phe Val Trp Met Trp Gly Val Lys Asn Leu Asp Leu
145                 150                 155                 160

Ser Gly Ile Ala Lys Ile Ser Leu Ser Val Gln Ser Ala Met His Asp
                165                 170                 175

Lys Thr Val Ile Ile Asp Asn Ile Arg Ile Gln Pro Asn Pro Pro Gln
                180                 185                 190

Asp Glu Asn Phe Leu Val Gly Leu Val Asp Glu Phe Gly Gln Asn Ala
                195                 200                 205

Lys Val Asp Tyr Lys Gly Lys Ile His Ser Leu Glu Glu Leu His Ala
210                 215                 220

Ala Arg Asp Val Glu Leu Ala Glu Leu Asp Gly Lys Pro Met Pro Ser
225                 230                 235                 240

Arg Ser Lys Phe Gly Gly Trp Leu Ala Gly Pro Lys Leu Lys Ala Thr
                245                 250                 255

Gly Tyr Phe Arg Thr Glu Lys Ile Asn Gly Lys Trp Met Leu Val Asp
                260                 265                 270

Pro Glu Gly Tyr Pro Tyr Phe Ala Thr Gly Leu Asp Ile Ile Arg Leu
                275                 280                 285

Ser Asn Ser Ser Thr Met Thr Gly Tyr Asp Tyr Asp Gln Ala Thr Val
290                 295                 300

Ala Gln Arg Ser Ala Asp Asp Val Thr Pro Glu Asp Ser Lys Gly Leu
305                 310                 315                 320

Met Ala Val Ser Glu Lys Ser Phe Ala Thr Arg His Leu Ala Ser Pro
                325                 330                 335

Thr Arg Ala Ala Met Phe Asn Trp Leu Pro Asp Tyr Asp His Pro Leu
                340                 345                 350

Ala Asn His Tyr Asn Tyr Arg Arg Ser Ala His Ser Gly Pro Leu Lys
                355                 360                 365

Arg Gly Glu Ala Tyr Ser Phe Tyr Ser Ala Asn Leu Glu Arg Lys Tyr
            370                 375                 380

Gly Glu Thr Tyr Pro Gly Ser Tyr Leu Asp Lys Trp Arg Glu Val Thr
385                 390                 395                 400

Val Asp Arg Met Leu Asn Trp Gly Phe Thr Ser Leu Gly Asn Trp Thr
                405                 410                 415

Asp Pro Ala Tyr Tyr Asp Asn Asn Arg Ile Pro Phe Phe Ala Asn Gly
                420                 425                 430

Trp Val Ile Gly Asp Phe Lys Thr Val Ser Ser Gly Ala Asp Phe Trp
                435                 440                 445

Gly Ala Met Pro Asp Val Phe Asp Pro Glu Phe Lys Val Arg Ala Met
            450                 455                 460

Glu Thr Ala Arg Val Val Ser Glu Glu Ile Lys Asn Ser Pro Trp Cys
465                 470                 475                 480
```

-continued

Val Gly Val Phe Ile Asp Asn Glu Lys Ser Phe Gly Arg Pro Asp Ser
              485                 490                 495

Asp Lys Ala Gln Tyr Gly Ile Pro Ile His Thr Leu Gly Arg Pro Ser
              500                 505                 510

Glu Gly Val Pro Thr Arg Gln Ala Phe Ser Lys Leu Leu Lys Ala Lys
              515                 520                 525

Tyr Lys Thr Ile Ala Ala Leu Asn Asn Ala Trp Gly Leu Lys Leu Ser
              530                 535                 540

Ser Trp Ala Glu Phe Asp Leu Gly Val Asp Val Lys Ala Leu Pro Val
545                 550                 555                 560

Thr Asp Thr Leu Arg Ala Asp Tyr Ser Met Leu Leu Ser Ala Tyr Ala
              565                 570                 575

Asp Gln Tyr Phe Lys Val Val His Gly Ala Val Glu His Tyr Met Pro
              580                 585                 590

Asn His Leu Tyr Leu Gly Ala Arg Phe Pro Asp Trp Gly Met Pro Met
              595                 600                 605

Glu Val Val Lys Ala Ala Ala Lys Tyr Ala Asp Val Val Ser Tyr Asn
              610                 615                 620

Ser Tyr Lys Glu Gly Leu Pro Lys Gln Lys Trp Ala Phe Leu Ala Glu
625                 630                 635                 640

Leu Asp Lys Pro Ser Ile Ile Gly Glu Phe His Ile Gly Ala Met Asp
              645                 650                 655

His Gly Ser Tyr His Pro Gly Leu Ile His Ala Ala Ser Gln Ala Asp
              660                 665                 670

Arg Gly Glu Met Tyr Lys Asp Tyr Met Gln Ser Val Ile Asp Asn Pro
              675                 680                 685

Tyr Phe Val Gly Ala His Trp Phe Gln Tyr Met Asp Ser Pro Leu Thr
              690                 695                 700

Gly Arg Ala Tyr Asp Gly Glu Asn Tyr Asn Val Gly Phe Val Asp Val
705                 710                 715                 720

Thr Asp Thr Pro Tyr Gln Glu Met Val Asp Ala Ala Lys Glu Val Asn
              725                 730                 735

Ala Lys Ile Tyr Thr Glu Arg Leu Gly Ser Lys
              740                 745

<210> SEQ ID NO 4
<211> LENGTH: 368
<212> TYPE: PRT
<213> ORGANISM: Saccharophagus degradans 2-40

<400> SEQUENCE: 4

Met Ser Asp Ser Lys Val Asn Lys Lys Leu Ser Lys Ala Ser Leu Arg
1               5                   10                  15

Ala Ile Glu Arg Gly Tyr Asp Glu Lys Gly Pro Glu Trp Leu Phe Glu
              20                  25                  30

Phe Asp Ile Thr Pro Leu Lys Gly Asp Leu Ala Tyr Glu Glu Gly Val
              35                  40                  45

Ile Arg Arg Asp Pro Ser Ala Val Leu Lys Val Asp Asp Glu Tyr His
              50                  55                  60

Val Trp Tyr Thr Lys Gly Glu Gly Glu Thr Gly Phe Gly Ser Asp
65                  70                  75                  80

Asn Pro Glu Asp Lys Val Phe Pro Trp Asp Lys Thr Glu Val Trp His
              85                  90                  95

Ala Thr Ser Lys Asp Lys Ile Thr Trp Lys Glu Ile Gly Pro Ala Ile

```
            100                 105                 110
Gln Arg Gly Ala Ala Gly Ala Tyr Asp Asp Arg Ala Val Phe Thr Pro
        115                 120                 125

Glu Val Leu Arg His Asn Gly Thr Tyr Tyr Leu Val Tyr Gln Thr Val
130                 135                 140

Lys Ala Pro Tyr Leu Asn Arg Ser Leu Glu His Ile Ala Ile Ala Tyr
145                 150                 155                 160

Ser Asp Ser Pro Phe Gly Pro Trp Thr Lys Ser Asp Ala Pro Ile Leu
                165                 170                 175

Ser Pro Glu Asn Asp Gly Val Trp Asp Thr Asp Glu Asp Asn Arg Phe
        180                 185                 190

Leu Val Lys Glu Lys Gly Ser Phe Asp Ser His Lys Val His Asp Pro
        195                 200                 205

Cys Leu Met Phe Phe Asn Asn Arg Phe Tyr Leu Tyr Tyr Lys Gly Glu
        210                 215                 220

Thr Met Gly Glu Ser Met Asn Met Gly Gly Arg Glu Ile Lys His Gly
225                 230                 235                 240

Val Ala Ile Ala Asp Ser Pro Leu Gly Pro Tyr Thr Lys Ser Glu Tyr
                245                 250                 255

Asn Pro Ile Thr Asn Ser Gly His Glu Val Ala Val Trp Pro Tyr Lys
                260                 265                 270

Gly Gly Met Ala Thr Met Leu Thr Thr Asp Gly Pro Glu Lys Asn Thr
        275                 280                 285

Cys Gln Trp Ala Glu Asp Gly Ile Asn Phe Asp Ile Met Ser His Ile
        290                 295                 300

Lys Gly Ala Pro Glu Ala Val Gly Phe Phe Arg Pro Glu Ser Asp Ser
305                 310                 315                 320

Asp Asp Pro Ile Ser Gly Ile Glu Trp Gly Leu Ser His Lys Tyr Asp
                325                 330                 335

Ala Ser Trp Asn Trp Asn Tyr Leu Cys Phe Phe Lys Thr Arg Arg Gln
                340                 345                 350

Val Leu Asp Ala Gly Ser Tyr Gln Gln Thr Gly Asp Ser Gly Ala Val
        355                 360                 365
```

<210> SEQ ID NO 5
<211> LENGTH: 30
<212> TYPE: DNA
<213> ORGANISM: Artificial Sequence
<220> FEATURE:
<223> OTHER INFORMATION: Forward primer, Aga16B-N

<400> SEQUENCE: 5
aaaggatcca tggcagattg ggacggaatt                                       30

<210> SEQ ID NO 6
<211> LENGTH: 34
<212> TYPE: DNA
<213> ORGANISM: Artificial Sequence
<220> FEATURE:
<223> OTHER INFORMATION: Reverse primer, Aga16B-C

<400> SEQUENCE: 6
aaagcggccg cgttgctaag cgtgaactta tcta                                  34

HEAT-RESISTANT AGARASE AND MONOSACCHARIDE PRODUCTION METHOD USING SAME

CROSS REFERENCE TO RELATED APPLICATIONS

This application is a National Stage of International Application No. PCT/KR2017/000561 filed Jan. 17, 2017, claiming priority based on Korean Patent Application No. 10-2016-0006589 filed Jan. 19, 2016.

BACKGROUND

1. Field of the Invention

The present invention relates to a heat-resistant agarase which improves the production yield of a reducing sugar consisting of galactose and 3,6-anhydro-L-galactose by using the heat-resistant agarase to efficiently break down agarose or agar without chemical pretreatment, a neutralization process, or an agarotriose hydrolase treatment process, and a monosaccharide production method using same.

2. Discussion of Related Art

A main polysaccharide constituting red algae is agarose, a polymer in which 3,6-anhydro-L-galactose and D-galactose are crossly linked by α-1,3 bonds and β-1,4 bonds. Agarose has characteristics of having low solubility in water at normal temperature and being dissolved in water at a high temperature, but becoming a hard gel while being cooled down. Due to these characteristics, there is a problem in that monosaccharides are obtained by breaking down agarose by only enzymatic saccharification.

In previous studies, the monosaccharides 3,6-anhydro-L-galactose and D-galactose were produced by saccharifying agarose with an exo-type β-agarase and an α-neoagarobiose hydrolase (NABH) after pretreatment through the chemical liquefaction of agarose by using acetic acid (3%) which is a weak acid in order to break down agarose (HT Kim et al., Bioresour. Technol. (2012) 107:301-306, HT Kim et al., Bioresour. Technol. (2013) 136:582-587). Whereby, the previous studies succeeded in increasing the yield of the monosaccharides obtained from agarose.

Further, recently, a process of obtaining monosaccharides by saccharifying agarose using an exo-type β-agarase, NABH, and an agarolytic β-galactosidase (C H Lee et al., Appl. Environ. Microbiol. (2014) 80:5965-5973) which is an enzyme which breaks down agarotriose which is a triose remaining as a byproduct after pretreatment at a high temperature together with an agar substrate by using a Tris-HCl butter (pH 7.4) which is a neutral buffer at low concentration instead of the weak acid has been developed (C H Lee et al., Process Biochem. (2015) 50: 1629-1633). The process has a benefit in that acetic acid, which is an expensive chemical catalyst, is not used, and an advantage in that formation of salts may be significantly reduced by minimizing a neutralization process.

However, a pretreatment method of using an acid or a buffer has a problem in that salts are formed or 5-hydroxymethylfurfural (5-HMF) is generated. In addition, since the pretreatment is performed at a high temperature (170° C. at the time of buffer pretreatment), a microwave apparatus or a high-temperature reactor needs to be used, which may become a big restriction in terms of a scale-up at the time of mass production and high costs of the device.

SUMMARY OF THE INVENTION

An object of the present invention is to provide a novel heat-resistant agarase capable of producing a reducing sugar at a high yield by an enzymatic cocktail including a heat-resistant agarase without chemical pretreatment in a hydrolysis reaction of agarose or agar at a high temperature, which is dissolved in water, and a use of an enzymatic cocktail including the same for producing monosaccharides.

In order to achieve the object, the present invention provides a composition for producing galactose or 3,6-anhydro-L-galactose, comprising: a heat-resistant agarase including an amino acid sequence of SEQ ID NO: 1; an exo-type agarase; and an α-neoagarobiose hydrolase.

The present invention also provides a method for producing galactose or 3,6-anhydro-L-galactose, the method comprising reacting agarose or agar as a substrate with the aforementioned composition for producing galactose or 3,6-anhydro-L-galactose.

The present invention has a simple process by effectively breaking down agarose or agar without existing chemical pretreatment, neutralization, agarotriose hydrolase treatment by using a heat-resistant agarase, and can produce galactose or 3,6-anhydro-L-galactose at high yield without any byproduct.

DETAILED DESCRIPTION OF EXEMPLARY EMBODIMENTS

Hereinafter, the composition of the present invention will be described in detail.

The present invention relates to a composition for producing galactose or 3,6-anhydro-L-galactose, comprising: a heat-resistant agarase including an amino acid sequence of SEQ ID NO: 1; an exo-type agarase; and an α-neoagarobiose hydrolase.

Further, the present invention provides a method for producing galactose or 3,6-anhydro-L-galactose, the method comprising reacting agarose or agar as a substrate with the aforementioned composition for producing galactose or 3,6-anhydro-L-galactose.

The present inventors have developed a processing method for producing 3,6-anhydro-L-galactose and D-galactose at high yield by applying a heat-resistant agarase Aga16B to a process to omit a chemical treatment process and allowing three enzymes (Aga16B, Aga50D, and NABH) to sequentially react with an agarose substrate to break down agarose through only enzymatic saccharification in order to improve a pretreatment method using acetic acid and a hot water pretreatment method using a Tris-HCl buffer (pH 7.4), which are known in the related art, and furthermore, solve a problem in that salts are generated during the neutralization process accompanying these pretreatment methods and a problem in that during the treatment process at a high temperature, 3,6-anhydro-L-galactose is excessively broken down into 5-HMF, and as a result, the saccharification yield is lowered.

Accordingly, galactose or 3,6-anhydro-L-galactose according to the present invention may be produced by reacting a heat-resistant agarase with agarose or agar, and then reacting reaction products obtained therefrom with an exo-type agarase and an α-neoagarobiose hydrolase.

Figure 10:
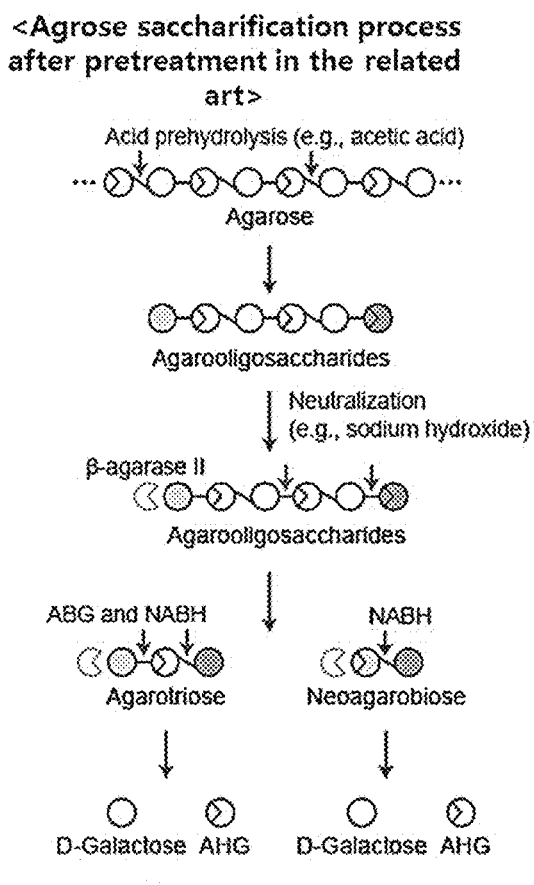
FIG. 10 is a schematic view illustrating the saccharification process of agarose by Aga16B, Aga50D, and NABH according to the related art and the present invention.
Figure 10:
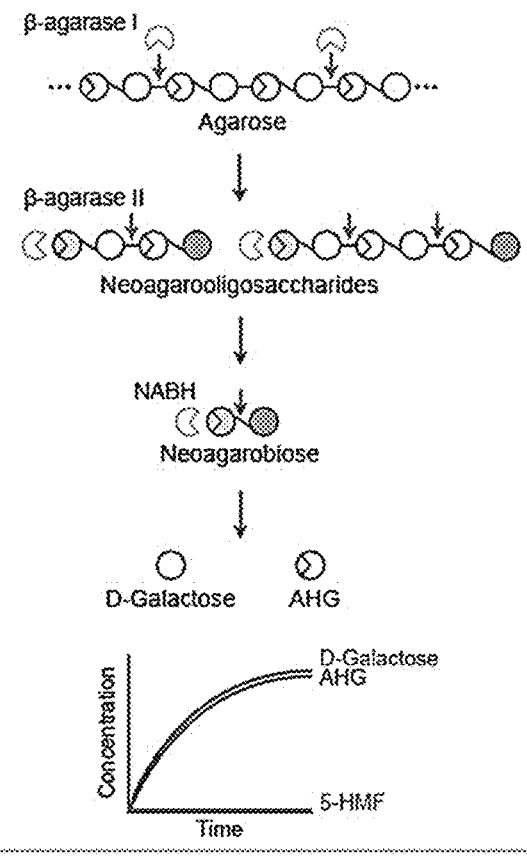

A method for producing 3,6-anhydro-L-galactose and D-galactose from agarose or agar by using a heat-resistant endo-type agarase, an exo-type agarase, and an α-neoagarobiose hydrolase without a weak acid or a buffer pretreatment process according to the present invention has the following benefits (see FIG. 10). 1) There is an effect of reducing costs because expensive acetic acid is not used. In addition, because 3,6-anhydro-L-galactose in the final breakdown products is a material which may also be used as a cosmetic functional material, the fact that acetic acid which induces an unpleasant odor is not used is one of the greatest advantages. 2) Salts such as sodium acetate produced through the neutralization process are not formed. 3) Since excessively broken down products such as 5-HMF are not produced, the yield of producing monosaccharides may be increased. 4) Since the existing chemical treatment process requires an apparatus such as a microwave, but an enzymatic process is carried out at a low temperature, a high-temperature adjusting apparatus is not required, so that there is a benefit in the scale-up. 5) When three types of enzyme groups are used, agarotriose is not produced as a breakdown product, so that an agarotriose hydrolase does not need to be used.

The heat-resistant agarase is an endo-type agarase, and the sol state of agarose in water in the enzymatic liquefaction of agarose may be more accessible to the enzyme than the gel state of agarose, so that as a result of evaluating a heat-resistant endo-type β-agarase, Aga16B as an agarose liquefaction enzyme, Aga16B maintains high thermal stability up to 50° C. exceeding a sol-gel transition temperature (~35° C.) of 1% (v/v) agarose in water, and more specifically, exhibits an optimal activity at about 55° C., and exhibits a breakdown activity of agarose or agar from room temperature to 60° C., so that Aga16B is characterized by being suitable for the enzymatic liquefaction of agarose at a relatively high temperature. Accordingly, Aga16B is characterized by being able to exhibit an activity within a temperature range in which agarose or agar is maintained in a liquid state, that is, at about 35° C. or more.

It was confirmed that the heat-resistant agarase uses agarose or agar as a substrate, and the enzymatic reaction products are neoagarotetraose and neoagarohexaose, which have a degree of polymerization (DP) of 4 and 6, respectively.

When an exo-type agarase and an α-neoagarobiose hydrolase, which are exo-type agarases, are sequentially treated, the heat-resistant agarase may exhibit a saccharification yield which is improved as compared to a saccharification yield obtained through chemical pretreatment in the related art. According to a specific exemplary embodiment, a saccharification yield increased by about 1.6 times (72.5% of theoretical maximum) as compared to the existing buffer pretreatment was obtained.

The heat-resistant agarase may be transcribed and translated through not only a region before and after a coding region of the enzyme, but also a DNA segment associated with the production of a polypeptide including an intervening sequence between individual coding segments, that is, a coding gene. For example, the heat-resistant agarase may be transcribed and translated from the sequence set forth in SEQ ID NO: 2, but is not particularly limited thereto. Further, a protein having a hydrolytic activity into the neoagarotetraose or the neoagarohexaose as a variant protein with one or more substitutions, deletions, translocations, additions, and the like of the enzyme is also included in the scope of rights of the enzyme of the present invention, and preferably, includes an amino acid sequence having a sequence identity of 80% or more, 85% or more, 90% or more, 93% or more, 94% or more, 95% or more, 96% or more, 97% or more, 98% or more, and 99% or more with the amino acid sequence set forth in SEQ ID NO: 1.

The heat-resistant agarase may be derived from *Saccharophagus degradans* 2-40$^T$, but is not particularly limited thereto.

The heat-resistant agarase may be separated and purified from a supernatant of the *Saccharophagus degradans* 2-40$^T$ culture, and may be produced and separated by a strain other than the *Saccharophagus degradans* 2-40$^T$ or an artificial chemical synthesis method, and the like by using genetic engineering recombinant technology. When the recombinant technology is used, the heat-resistant agarase may be used by replacing a supernatant or supernate fluid of the transformed *E. coli* culture by transforming *E. coli*, but the method is not particularly limited thereto. According to a specific exemplary embodiment, the heat-resistant agarase may be obtained from *E. coli* transformed with a recombinant vector including the base sequence set forth in SEQ ID NO: 2, or a culture thereof.

The heat-resistant agarase and agarose or agar may produce neoagarotetraose or neoagarohexaose by reacting at a pH of 5 to 9 under a condition of 0 to 300 rpm within a temperature range of 40° C. to 60° C. for 30 minutes to 7 days.

The exo-type agarase is an enzyme which breaks down agarooligosaccharides into disaccharides neoagarobiose and agarotriose (D-galactose-β-1,4 linkage-3,6-anhydro-L-galactose-α-1,3 linkage-D-galactose), and an enzyme (hereinafter, also referred to as 'Aga50D') that cleaves a β-1,4-glycosidic bond between D-galactose and 3,6-anhydro-L-galactose in agarose.

For the exo-type agarase, not only the amino acid sequence set forth in SEQ ID NO: 3, but also a protein having the agarooligosaccharide hydrolytic activity as a variant protein with one or more substitutions, deletions, translocations, additions, and the like of the enzyme are included in the right scope of rights of the enzyme of the present invention, and preferably, the exo-type agarase may include the amino acid sequence set forth in SEQ ID: 3 and an amino acid sequence having a sequence identity of 80% or more, 85% or more, 90% or more, 93% or more, 94% or more, 95% or more, 96% or more, 97% or more, 98% or more, and 99% or more with the sequence.

The exo-type agarase may be derived from *Saccharophagus degradans* 2-40$^T$, but is not particularly limited thereto.

The exo-type agarase may be separated and purified from a supernatant of the *Saccharophagus degradans* 2-40$^T$ culture, and may be produced and separated by a strain other than the *Saccharophagus degradans* 2-40$^T$ or an artificial chemical synthesis method, and the like by using genetic engineering recombinant technology.

When the recombinant technology is used, in order to facilitate typical recombinant protein expression, for example, it is possible to use factors such as an antibiotic resistance gene, and a reporter protein or peptide which may be used for affinity column chromatography, and the technology corresponds to a scope which the person skilled in the art to which the present invention pertains can easily carry out. For example, the exo-type agarase may be used as a replacement for a supernatant of the transformed yeast culture by transforming an edible strain, for example, yeast. For a more specific preparation technique, Korean Patent Application Laid-Open No. 2010-0040438 (Apr. 20, 2010) may be referenced.

The reaction of the agarooligosaccharide with the exo-type agarase may be carried out within a temperature range of 20 to 40° C. for 30 minutes to 7 days. More specifically, the reaction may be carried out within a temperature range of 25 to 35° C. for 1 day to 4 days.

For an α-neoagarobiose hydrolase (also referred to as 'SdNABH') which may break down the neoagarobiose into 3,6-anhydro-L-galactose and D-galactose, not only the amino acid sequence set forth in SEQ ID NO: 4, but also a protein having the neoagarobiose hydrolytic activity as a variant protein with one or more substitutions, deletions, translocations, additions, and the like of the enzyme are included in the scope of rights of the enzyme of the present invention, and preferably, the α-neoagarobiose hydrolase includes an amino acid sequence having a sequence identity of 80% or more, 85% or more, 90% or more, 93% or more, 94% or more, 95% or more, 96% or more, 97% or more, 98% or more, and 99% or more with the amino acid sequence set forth in SEQ ID NO: 4.

The α-neoagarobiose hydrolase may be derived from *Saccharophagus degradans* 2-40$^T$, but is not particularly limited thereto.

The α-neoagarobiose hydrolase may be separated and purified from a supernatant or supernate fluid of the *Saccharophagus degradans* 2-40$^T$ culture, and may be produced and separated by a strain other than the *Saccharophagus degradans* 2-40$^T$ or an artificial chemical synthesis method, and the like by using genetic engineering recombinant technology. For a more specific preparation technique, Korean Patent Application Laid-Open No. 2013-0085017 (Jul. 26, 2013) may be referenced.

The reaction of the neoagarobiose with the α-neoagarobiose hydrolase may be carried out within a temperature range of 20 to 40° C. for 30 minutes to 7 days. More specifically, the reaction may be carried out within a temperature range of 25 to 35° C. for 1 day to 4 days.

For a breakdown product of the neoagarobiose, 3,6-anhydro-L-galactose at a high purity of approximately 95% may be separated and purified by sequentially carrying out silica gel chromatography which is adsorption chromatography and Bio-Gel P2 chromatography which is gel permeation chromatography.

In the present specification, "protein" and "polypeptide" are used interchangeably.

In the present invention, the fact that a polypeptide has a sequence identity of a specific ratio (for example, 80%, 85%, 90%, 95%, or 99%) with another sequence means that when the two sequences are aligned, the amino acid residues at the ratio are the same as each other at the time of comparing the sequences. The alignment and percentage homology or identity may be determined by using those described in any suitable software program publicly known in the art, for example, a document [CURRENT PROTOCOLS IN MOLECULAR BIOLOGY (F. M. Ausubel et al., (eds) 1987 Supplement 30 section 7.7.18)]. Examples of a preferred program include a GCG Pileup program, FASTA (Pearson et al., 1988 Proc. Natl Acad. Sci USA 85:2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR25:3389-3402). Another preferred alignment program is ALIGN Plus (Scientific and Educational Software, PA), and preferably, default parameters are used. Another available sequence software program is the TFASTA Data Searching Program available in the Sequence Software Package Version 6.0 (Genetics Computer Group, University of Wisconsin, Madison, Wis.).

In the present invention, the term "recombinant" when used in connection with a cell, a nucleic acid, a protein, or a vector indicates that the cell, the nucleic acid, the protein, or the vector has been modified by introducing a heterologous nucleic acid or protein or changing an original nucleic acid or protein, or that the cell is derived from the thus modified cell. That is, for example, a recombinant cell expresses a gene which is not found within the original (non-recombinant) form of the cell, or otherwise, the recombinant cell expresses an original gene which is abnormally expressed or not expressed at all during expression.

In the present specification, "nucleic acid" encompasses single stranded or double stranded DNA and RNA, and a chemical variant thereof. "Nucleic acid" and "polynucleotide" may be used interchangeably in the present application. Since the genetic code is degenerate, one or more codons may be used in order to encode a specific amino acid, and the present invention encompasses a polynucleotide encoding a specific amino acid sequence.

The term "introduction" in which a nucleic acid sequence is inserted into a cell means "transfection", or "transformation" or "transduction", and a reference to the integration of a nucleic acid sequence into an eukaryotic cell or a prokaryotic cell is included, and in this case, the nucleic acid sequence is integrated into a genome (for example, a chromosome, a plasmid, a plastid, or a mitochondrial DNA) of a cell, and thus is converted into an autonomous replicon, or transiently expressed.

Hereinafter, the present invention will be described in more detail through the Examples according to the present invention, but the scope of the present invention is not limited by the Examples suggested below.

<Example 1> Measurement of Sol-Gel Phase Transition of Agarose by Cooling

In order to observe the temperature interval in which agarose in a solution state of being dissolved in water at a high temperature is changed into a gel state while decreasing the temperature, the sol-gel phase transition of agarose was measured by using specific optical rotation while cooling the agarose from 80° C. to 10° C. after 1% (w/v) agarose at the time of cooling was dissolved in a 20 mM Tris-HCl buffer (pH 7.0).

Figure 1:
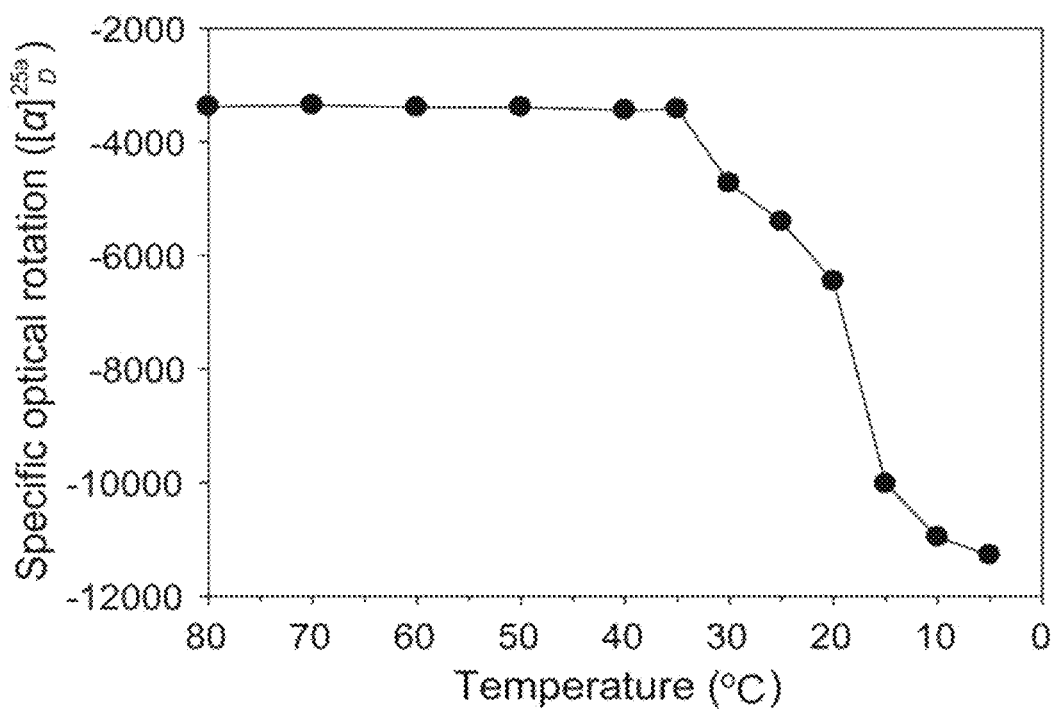
FIG. 1 is a sol-gel phase transition analysis result of agarose, which is confirmed while 1% agarose is cooled down.

As illustrated in FIG. 1, it could be confirmed that agarose was gelled at a temperature less than 35° C.

<Example 2> Cloning and Expression of Aga16B

After an endo-type β-agarase aga16B gene (Sde_1175: UniProt accession no. Q21112) from a marine bacterium *Saccharophagus degradans* 2-40 was introduced into *E. coli* by being cloned into a pET21a plasmid, an overexpressed Aga16B enzyme was purified and used in an enzymatic reaction.

For this purpose, genomic DNA was purified by using a commercial DNA kit (Bioneer, Korea), and Aga16B was amplified by PCR. In this case, the primers were Aga16B-N, 5-AAA GGATCC ATGGCAGATTGGGACGGAATT-3 (Tm: 59.4)(SEQ ID NO: 5); and Aga16B-C, 5-AAA GCG-GCCGC GTTGCTAAGCGTGAACTTATCTA-3 (Tm: 59.3)(SEQ ID NO: 6).

The PCR product was a product in which a signal sequence positioned at amino acids 19-20 at the N-terminus of Aga16B was removed. BamHI and NotI were used as restriction enzymes, and were positioned at the 5 and 3 regions of the N- and C-terminal ends. The PCR product and pET21a were digested with BamHI and NotI, respectively, and ligated together using a T4 DNA ligase. And then, the resulting vector was transformed into BL21 *E. coli*.

In order to produce recombinant proteins from each gene, the transformed *E. coli* was inoculated into a medium containing 50 m/mL of ampicillin, and grown at 37° C. When the transformed *E. coli* was grown until the mid-exponential phase, protein expression was induced at 16° C. for 16 hours after adding 0.1 mM isopropyl-β-D-thiogalactopyranoside (IPTG). Thereafter, the cells were harvested by centrifugation at 8,000 rpm for 20 minutes at 4° C., and then were resuspended in a lysis buffer (20 mM sodium phosphate and 500 mM sodium chloride, pH 7.4), and the cells were disrupted using a sonicator. The cells were centrifuged at 16,000 rpm for 1 hour at 4° C. After the protein was purified by using a His-Trap column (GE Healthcare) and concentrated by using an Amicon ultrafiltration membrane, the Aga16B protein was identified by SDS-PAGE. The concentration of Aga16B was measured using a BCA protein assay kit.

Figure 2:
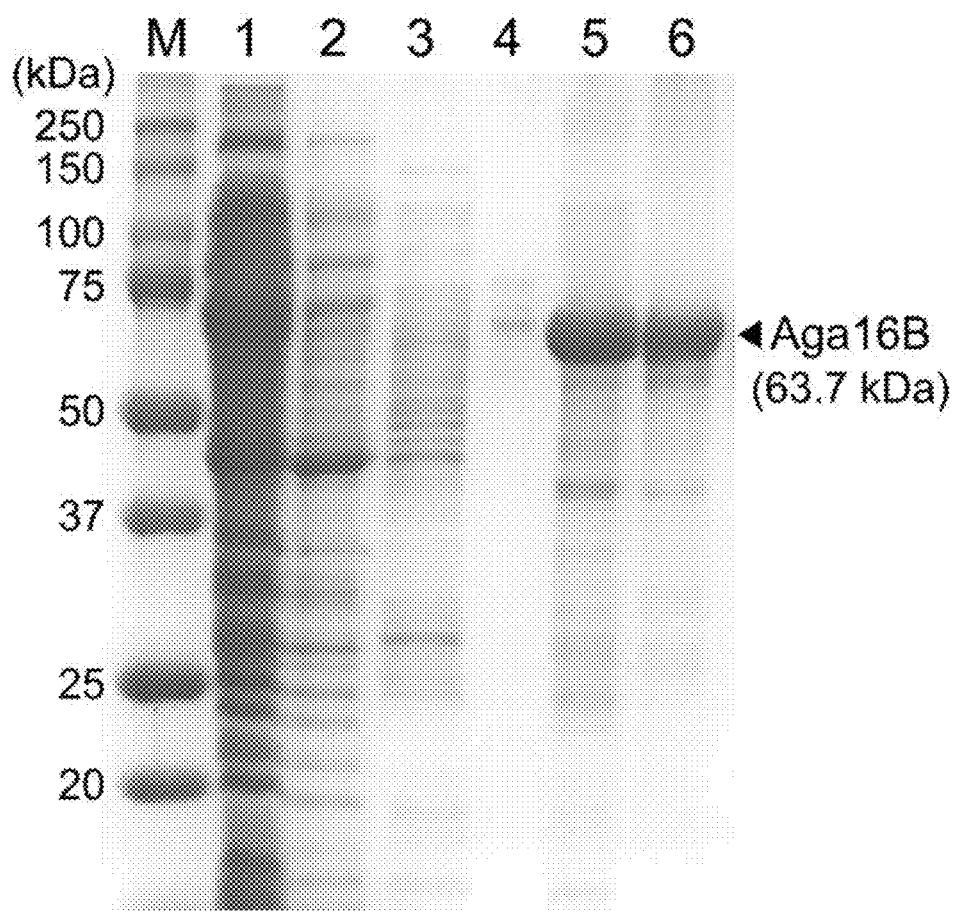
FIG. 2 is an SDS-PAGE result in which Aga16B is overexpressed and purified, Line M indicates a protein ladder, Line 1 indicates a crude protein, Line 2 indicates a sample circulating a His-Trap column and exiting the His-Trap column, Line 3 indicates a sample flowing in a column with an EQ buffer, and Lines 4, 5, and 6 indicate purified Aga16B.

As illustrated in FIG. 2, a band with a size of 63.7 kDa corresponding to Aga16B was identified.

<Example 3> Measurement of Activity, Optimal pH and Temperature of Aga16B

A substrate was produced by dissolving 1% (w/v) agarose in 3 mL of a 20 mM Tris-HCl buffer (pH 7.0) in an autoclave at 121° C. for 10 minutes, and then 0.0625 μmol of an Aga16B protein was added thereto, and the resulting mixture was allowed to react at 200 rpm for 30 minutes at 45° C.

Further, the optimal reaction temperature and pH of Aga16B were monitored. For an optimal temperature experiment, a substrate was produced by putting 1% (w/v) agarose into a 20 mM Tris-HCl buffer (pH 7.0) and dissolving the agarose at 121° C. for 10 minutes, the Aga16B overexpressed in Example 2 was purified while cooling the substrate from 70° C. to 30° C. and was put into the substrate so as to be at a concentration of 4 mg/g agarose, and the resulting mixture was allowed to react at 200 rpm.

For an optimal pH experiment, agarose was produced so as to be at a concentration of 1% (w/v) in each buffer by using a 20 mM sodium phosphate buffer (pH 5 to 7), a 20 mM Tris-HCl buffer (pH 7.5 to 9), and a 20 mH borate buffer (pH 9.5 to 11), and then a substrate was produced by dissolving the agarose in an autoclave at 121° C. for 10 minutes, an amount of protein, which is the same as that in the optimal temperature experiment, was added thereto, and the resulting mixture was allowed to react at 200 rpm for 30 minutes at 45° C.

For all of the three experiments, after the protein was inactivated at 95° C. for 1 minute after a protein reaction, a supernatant was produced by centrifugation at 16,000 rpm for 10 minutes, the supernatant was mixed with a dinitrosalicylic acid (DNS) reagent at a ratio of 1:1, the resulting mixture was allowed to react at 95° C. for 5 minutes, and then a reducing sugar of a reaction product was measured by measuring an absorbance at 540 nm using a microplate reader. In this case, galactose was used as a standard material.

Figure 3A:
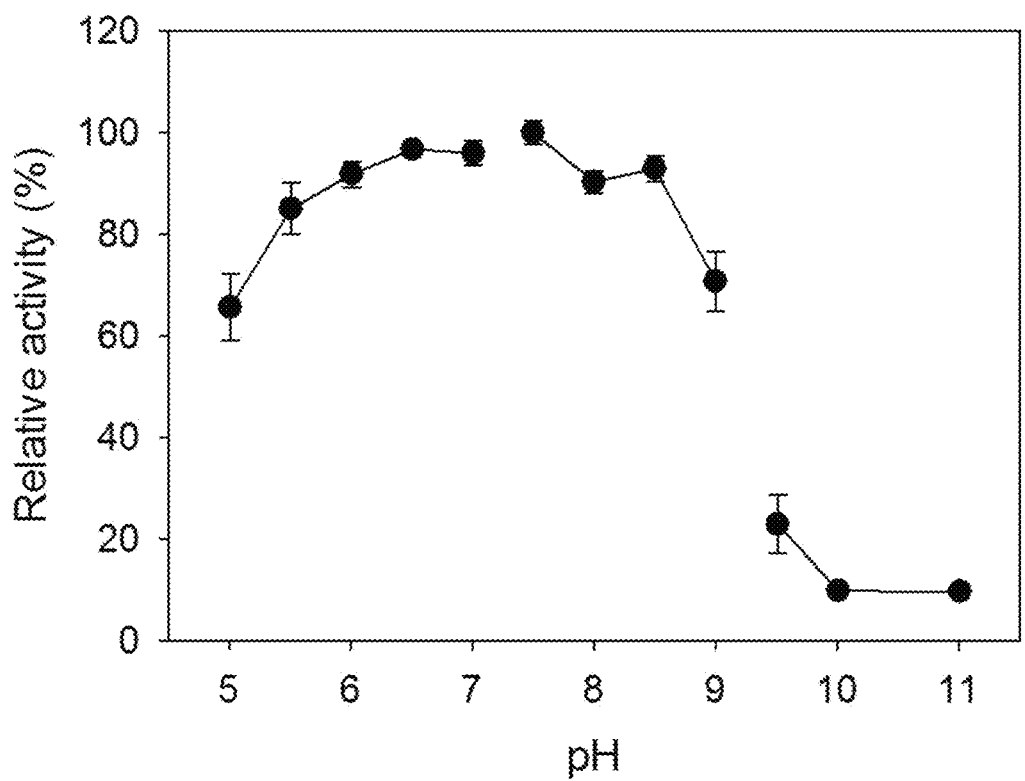
FIG. 3a is a result of measuring an optimal pH of Aga16B.
Figure 3B:
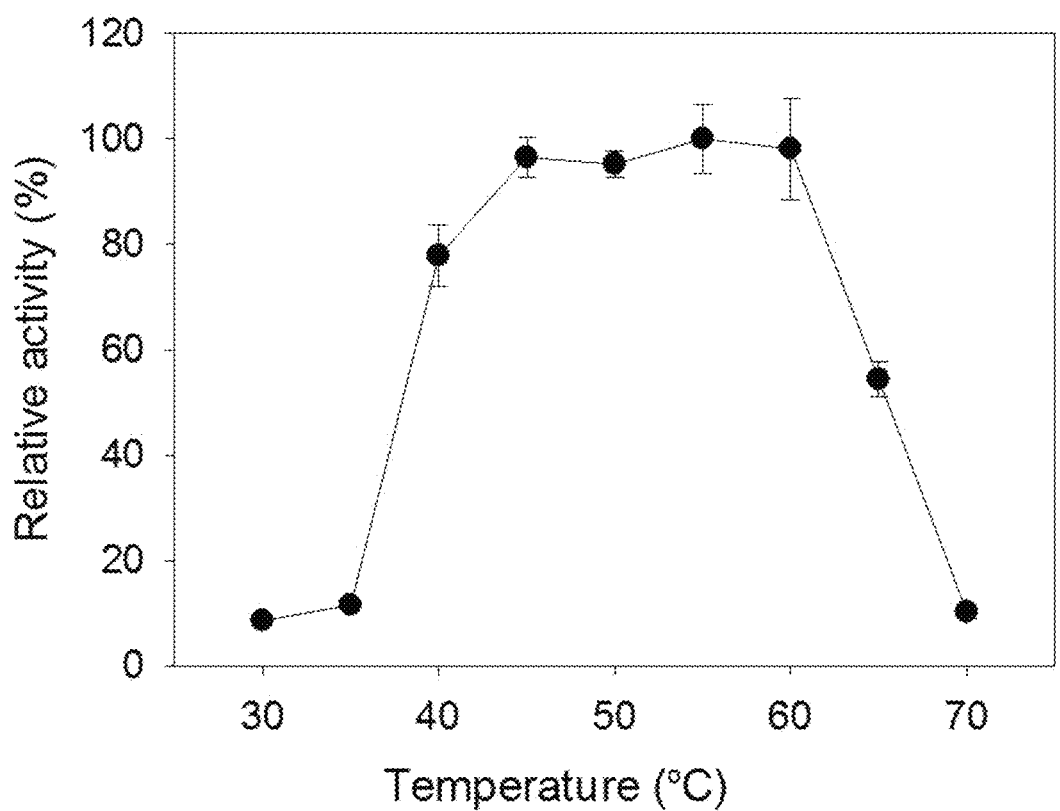
FIG. 3b is a result of measuring an optimal reaction temperature of Aga16B.

As illustrated in FIG. 3a, the optimal pH of Aga16B was 7.5, but high activity was exhibited within a wide range from pH 5.5 to pH 8.5 similarly to the temperature. Further, as in FIG. 3b, it was shown that the enzyme had activity at a temperature of 40° C. or more where agarose is present in a sol (liquid) state, and the activity of the enzyme was shown to be high up to 60° C. In addition, the optimal temperature of the enzyme was shown to be 55° C., and high enzymatic activity was shown to be maintained within a wide range from 40° C. to 60° C.

<Example 4> Thermal Stability Experiment of Aga16B

In order to carry out a thermal stability experiment of Aga16B, a substrate was produced by introducing a 20 mM Tris-HCl buffer (pH 7.0) and a 1% (w/v) agarose substrate and then dissolving using an autoclave at 121° C. for 10 minutes, and then the Aga16B protein was pre-incubated at 40° C., 45° C., 50° C., 55° C., 60° C., and 65° C., Aga16B was added thereto so as to be at a concentration of 4 mg/g agarose, and then a reducing sugar of a reaction product was measured through the DNS reaction by performing sampling at 0, 10, 20, 30, 60, 90, and 120 minutes while allowing the resulting mixture to react at 45° C. and 200 rpm.

Figure 4:
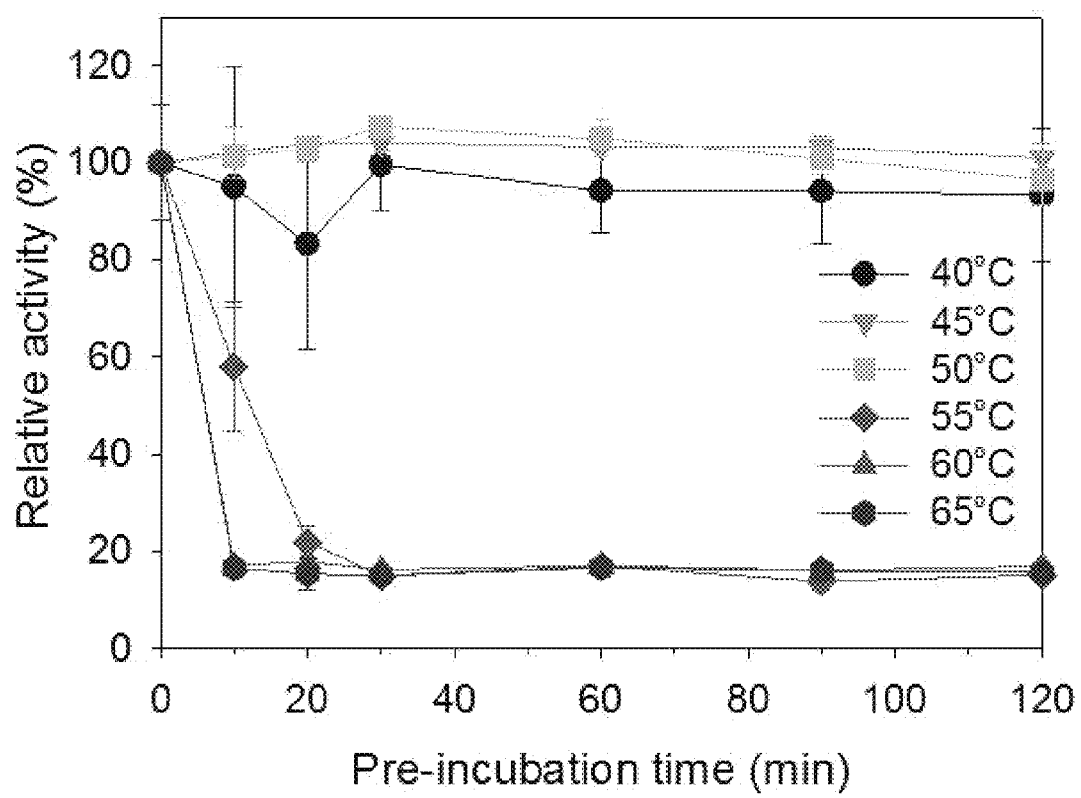
FIG. 4 is a result of an experiment on stability of Aga16B at various temperatures.

As illustrated in FIG. 4, it could be confirmed that the Aga16B was stable at 40° C., 45° C., and 50° C., and the enzymatic activity was decreased at 55° C. or more within 30 minutes by less than 20% as compared to the initial level, and as a result, the stability deteriorated.

<Example 5> Measurement of Suitable Aga16B Protein-Loading Amount

Since a loading amount of an enzyme needs to be determined in order to apply the Aga16B protein to a process, an experiment of measuring a suitable loading amount was carried out.

A suitable Aga16B-loading amount was measured under enzymatic reaction conditions of a 1% (w/v) agarose substrate, pH 7.0, and 45° C. and the initial reaction rates were compared by varying the Aga16B-loading amount.

Figure 5:
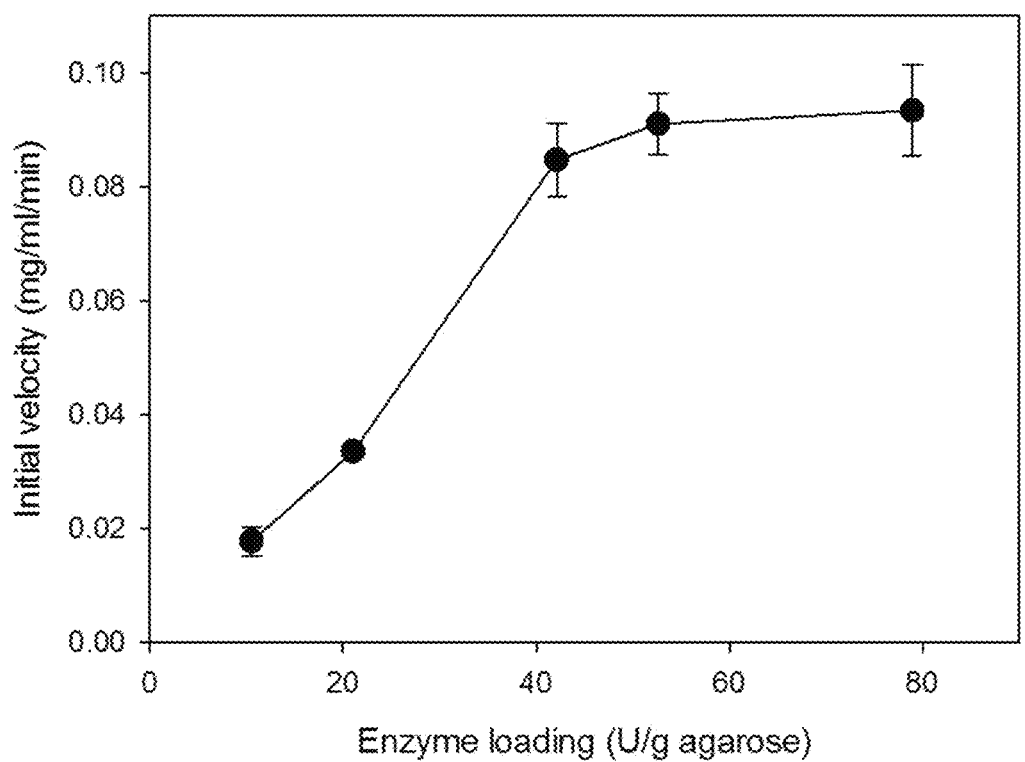
FIG. 5 is a result illustrating an effect of an Aga16B protein-loading amount according to initial rate.

As illustrated in FIG. 5, the initial rate obtained by Aga16B increased until the enzyme loading of Aga16B was increased to 42 U/g agarose. Even though the amount of Aga16B loaded was increased to an Aga16B-loading amount higher than 42 U/g agarose, the initial rate of the enzymatic reaction was almost constantly maintained. As a result of the present experiment, the Aga16B loading at 42 U/g agarose was the same as that at 8 mg Aga16B/g agarose.

<Example 6> Effects of Metal Ions on Enzymatic Activity of Aga16B

Effects of metal ions on the enzymatic activity of Aga16B were tested by selecting 0.1% (w/v) agarose as a substrate and one of various metal ions.

As shown in Table 1, most ions did not affect the enzymatic activity of Aga16B, but $CuCl_2$ and $FeCl_2$ significantly decreased the enzymatic activity of Aga16B to 76.6% and 82.6% of the maximum activity, respectively.

TABLE 1

Effects of Metal Ions on Relative Activity of Aga16B

| Metal salt | Relative activity % |
|---|---|
| Control[a] | 100.0 ± 0.3 |
| $CuCl_2$ | 76.6 ± 0.6 |
| $MgCl_2$ | 99.1 ± 0.1 |
| $MnCl_2$ | 93.4 ± 0.5 |
| $CaCl_2$ | 96.5 ± 0.2 |
| $FeCl_2$ | 82.6 ± 0.7 |
| $NH_4Cl$ | 97.9 ± 0.1 |
| KCl | 96.8 ± 0.3 |
| NaCl | 93.0 ± 0.3 |

[a]The enzymatic activity when a metal ion was not present was set to 100%. The experimental value was expressed as average ± standard deviation obtained from triplicate experiments.

<Example 7> Kinetic Parameters of Aga16B

In order to measure the kinetic parameters of Aga16B, an enzymatic reaction was performed at a pH of 7.0 and 45° C. in 3 mL of the entire reaction mixture volume including 0.04 mg/mL of purified Aga16B per concentration of agarose (0.5% to 2% (w/v)). The reaction time was 6 minutes for 0.5% and 1% (w/v) agarose and 10 minutes for 1.5% and 2% (w/v) agarose. The $V_{max}$ and $K_m$ were calculated from the Lineweaver-Burk plot. And then, these kinetic constants of Aga16B were compared with those of other β-agarases belonging to GH16, that is, β-agarases, originating from marine bacteria such as Streptomyces coelicolor, Microbulbifer elongatus JAMB-A7, and Agarivorans albus YKE-34.

As shown in Table 2, the $K_m$ value of Aga16B with respect to agarose was 7.7 mg/ml, which was 38.5 times higher than that of AgaB34 and 3.5 times higher than that of DagA, respectively. The $V_{max}$ value of Aga16B was 18.3 U/mg proteins, which was 2.7 times lower than that of AgaB34. When compared to other β-agarases belonging to GH16, Aga16B showed the lowest value of $K_{cat}$ (that is, 20 s$^{-1}$). Therefore, the catalytic efficiency (that is, $K_{cat}/K_m$) of Aga16B was relatively low as compared to those of other β-agarases of GH16.

TABLE 2

Comparison of the kinetic parameters of Aga16B with the known agarases belonging to GH16

| Agarase | Organism | Substrate | Product | $V_{max}$ (U/mg protein) | $K_m$ (mg/mL) | $k_{cat}$ (s$^{-1}$) | $k_{cat}/K_m$ (s$^{-1}$/mg/mL) | Reference |
|---|---|---|---|---|---|---|---|---|
| Aga16B | S. degradans 2-40$^T$ | Agarose | DP4, DP6 | 18.3 | 7.7 | 2.0 × 10$^1$ | 2.6 × 10$^1$ | This invention |
| AgaB34 | Agarivorans albus YKW-34 | Agarose | DP4 | 50.0 | 0.2 | 4.1 × 10$^1$ | 2.1 × 10$^2$ | Fu et al. J Microbiol Biotechnol 19(3): 257-264, 2009 |
| DagA | Streptomyces coelicolor | Agarose | DP4, DP6 | 39.0 | 2.2 | 9.5 × 10$^3$ | 4.3 × 10$^3$ | Temuujin U et al. Appl Microbiol Biotechnol 92(4): 749-759, 2011 |
| AgaA7 | Microbulbifer elongatus JAMB-A7 | Agar | DP4 | N.A. | 3.0 | 2.9 × 10$^6$ | 9.6 × 10$^5$ | Ohta et al. Appl Microbiol Biotechnol 64(4): 505-514, 2004 |

N.A.: not available

<Example 8> Product Analysis of Enzymatic Reaction Products of Aga16B

In order to monitor the enzymatic reaction products of Aga16B, TLC and HPLC analyses were carried out. For the TLC, 1 µl of the enzymatic reaction products was loaded onto a silica gel plate, eluted in a mobile phase in which n-butanol, ethanol, and water were mixed at a volume ratio of 3:1:1 (v/v/v), and then was color-developed by using 10% sulfuric acid and 0.2% 1,3-dihydroxynaphthalene. For the HPLC analysis, the reaction product samples obtained at a reaction time of 0, 2, 10, and 30 minutes were analyzed under a column temperature condition of 80° C. and at a flow rate of 0.5 mL/min by using a KS-802 column (Shodex).

Figure 6A:
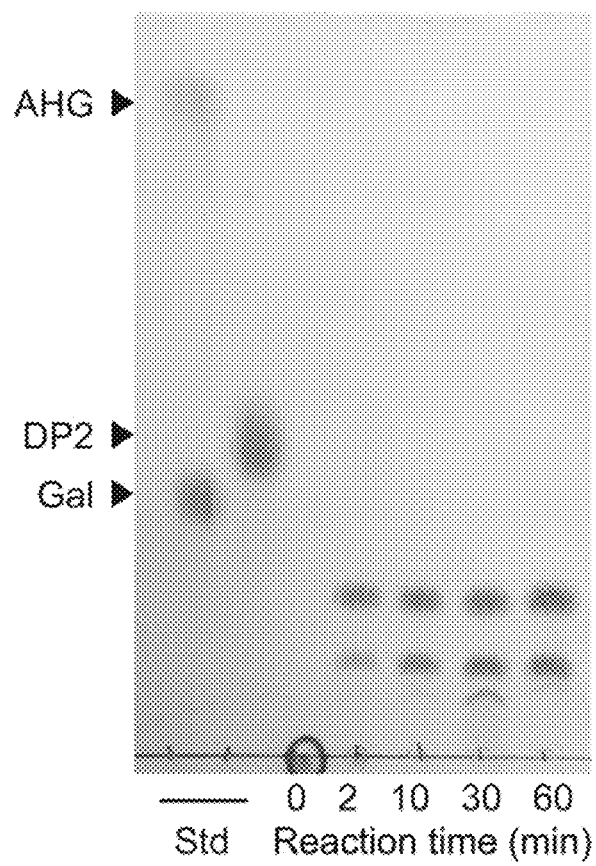
FIG. 6a is a TLC analysis result of Aga16B reaction products.
Figure 6B:
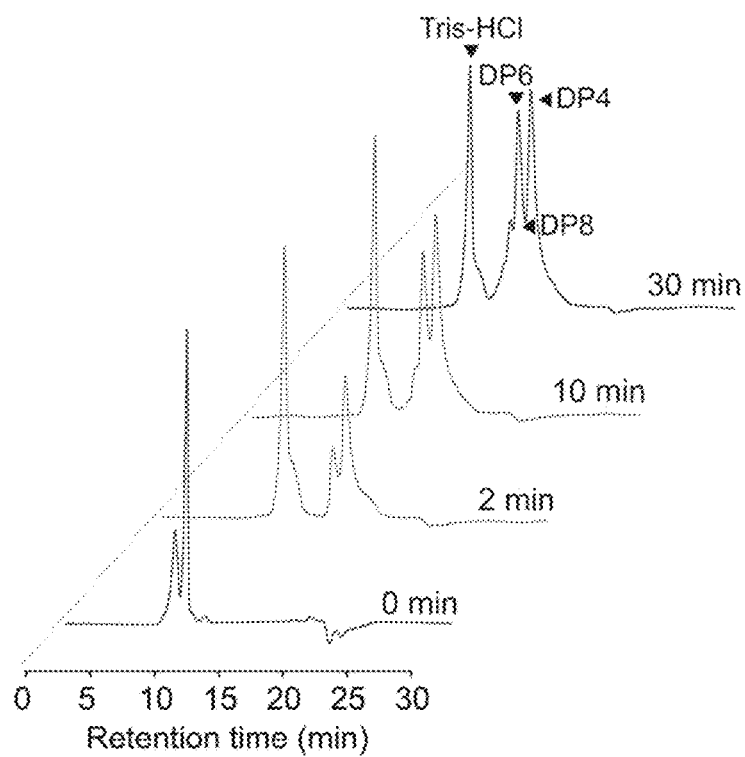
FIG. 6b is an HPLC analysis result of Aga16B reaction products.

As illustrated in FIG. 6a, it could be confirmed that as a result of TLC, the reaction products were formed after a reaction time of 2 minutes, and as in FIG. 6b, it could be confirmed that through the HPLC analysis, the reaction products were neoagarotetraose and neoagarohexaose, which is DP4 and DP6, respectively. And, DP8 was detected as a minor product.

In order to identify exact masses of the enzymatic reaction products by Aga16B, an MALDI-TOF/TOF MS analysis was performed. The MALDI-TOF/TOF MS is an ultrafleXtreme MALDI-TOF/TOF MS system (Bruker Daltonics, Bremen, Germany). The salts and buffer were removed by purifying the reaction products of Aga16B through solid-phase extraction using a porous graphitized carbon cartridge prior to the analysis (Thermo Fisher Scientific, San Jose, Calif., USA). The purified reaction products were re-dissolved in water, 1 µL of the reaction products was spotted on a stainless steel target plate, and then 0.5 µL of 0.1 mg/mL 2,5-dihydroxy-benzoic acid dissolved in 0.3 µl of 0.01 M NaCl and 50% acetonitrile was spotted. A homogeneous crystal was formed by drying the spot under vacuum. The MALDI-TOF mass spectra were acquired in a positive mode over the m/z range from 500 to 3000 for a total of 2400 laser shots. To obtain MS/MS data, precursor ions were accelerated to 7.5 kV and selected in a time ion selector for fragment ion analysis in the TOF/TOF mode. Fragment ions generated by 1 keV collision energy via collision-induced dissociation (CID) of precursor ions were further accelerated by 19 kV in the LIFT cell, and their masses were analyzed after having them pass through the ion reflector. Argon was used as a collision gas at a pressure of $5.9 \times 10^{-6}$ mbar. Raw MS data and MS/MS data were processed using the flex-Analysis software (Version 3.3, Bruker Daltonics, Bremen, Germany)

Figure 7A:
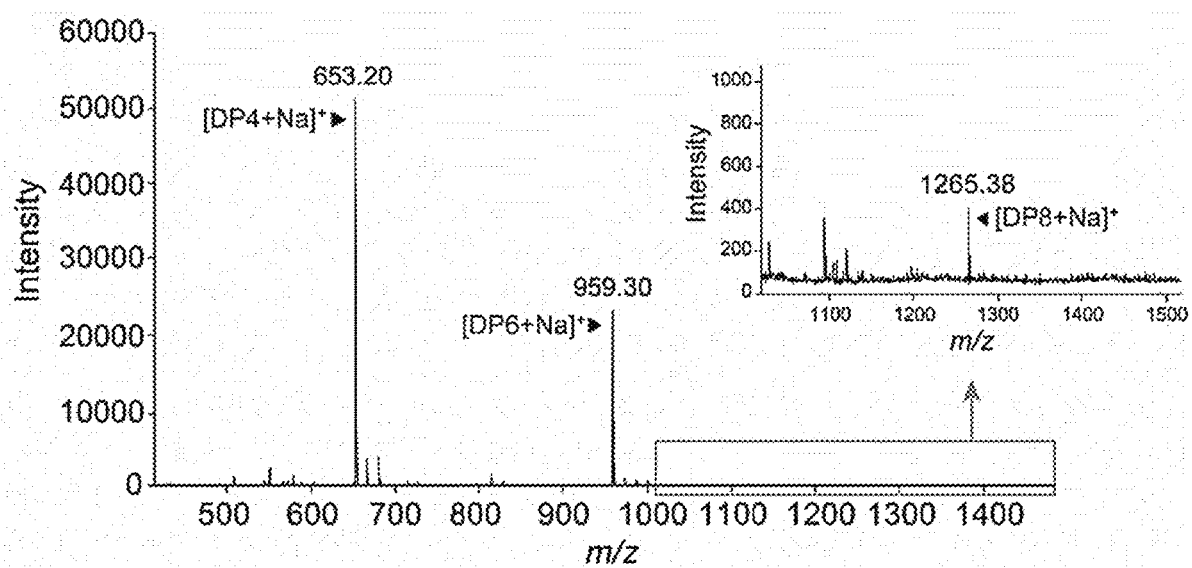
FIG. 7a illustrates a MALDI-TOF/TOF MS confirmation result of reaction products of Aga16B.

As illustrated in FIG. 7a, the exact masses of the main reaction products of Aga16B and agarose were measured as 653.2 and 959.3, respectively, which correspond to neoagarotetraose (DP4) and neoagarohexaose (DP6), respectively. Meanwhile, neoagarooctaose (DP8) with a mass of 1,265.4 was also detected as a minor product.

Figure 7B:
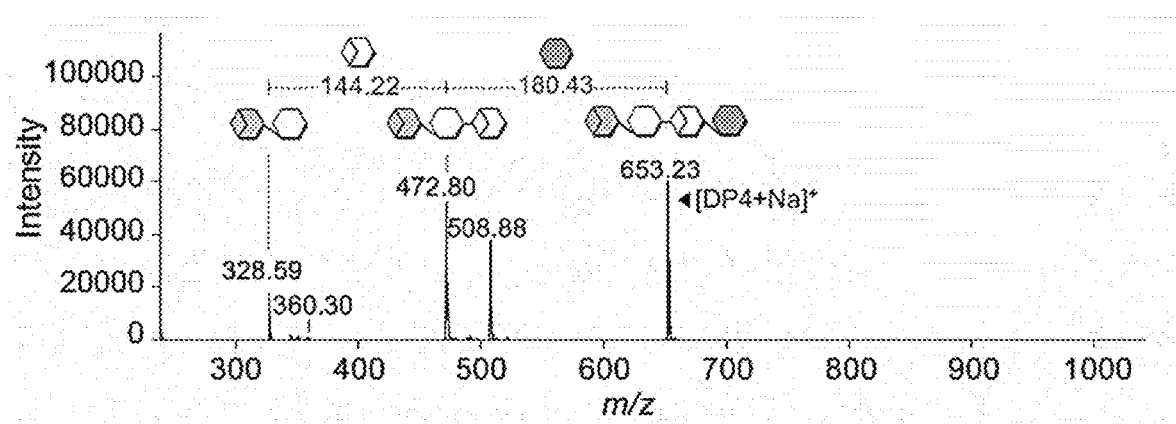
FIG. 7b illustrates a tandem MS analysis result of DP4 which is a reaction product of Aga16B.
Figure 7C:
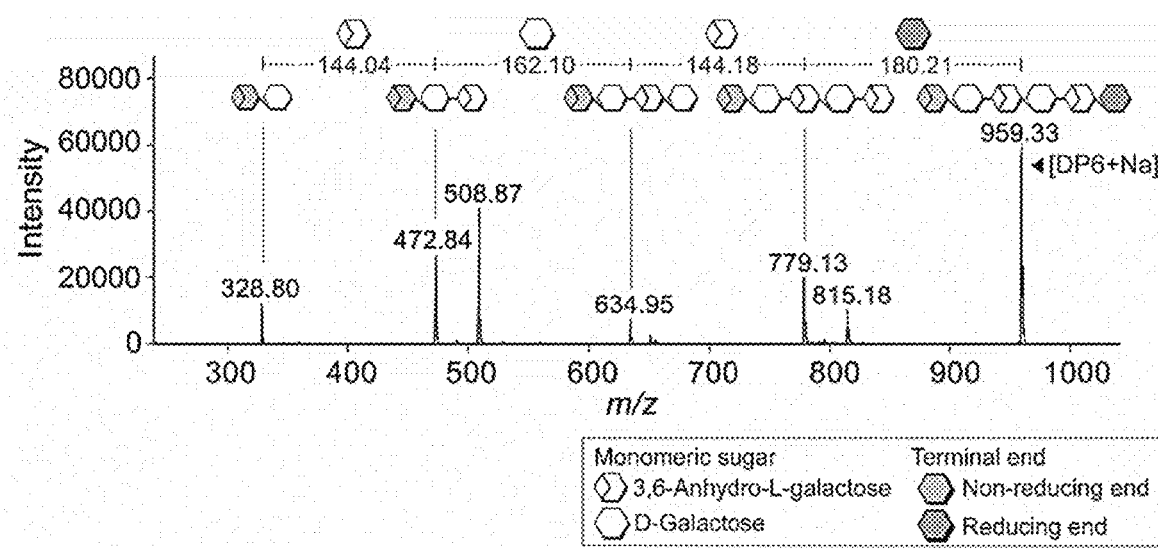
FIG. 7c illustrates a tandem MS analysis result of DP6 which is a reaction product of Aga16B.

Additionally, as a result of performing tandem MS for the analysis of the chemical structures of the main reaction products, neoagarotetraose and neoagarohexaose were confirmed, as illustrated in FIG. 7b and FIG. 7c. Specifically, the daughter ions produced from the precursor ions of neoagarotetraose and neoagarohexaose demonstrated that these reaction products consist of AHG and galactose, being bonded by alternating glycosidic bonds.

<Example 9> Experiment of Confirming Liquefaction of Agarose Broken Down by Aga16B To monitor the liquefaction degree of the reaction products by Aga16B, the absorbance for the agarose substrate, the Aga16B reaction products, and the 20 mM Tris-HCl buffer (pH 7.0) was measured.

For this purpose, the absorbance was measured at 600 nm by using a product which caused the enzymatic reaction using a substrate in which 1% (w/v) agarose was dissolved in a 20 mM Tris-HCl buffer (pH 7.0) and an Aga16B protein and using a spectrophotometer, and the liquefaction degree was confirmed through the transparency. In this case, the substrate in which 1% (w/v) agarose was dissolved in a 20 mM Tris-HCl buffer (pH 7.0) was autoclaved at 121° C. for 10 minutes, and then cooled at room temperature, and the product obtained by allowing the Aga16B protein and the substrate to react with each other was a supernatant obtained by allowing the substrate in which 1% agarose dissolved in the 20 mM Tris-HCl buffer (pH 7.0) was autoclaved at 121° C. for 10 minutes to react with the protein at 45° C. for 30 minutes, and then inactivating the protein in boiling water at 95° C. or more, and performing centrifugation at 16,000 rpm for 10 minutes.

Figure 8:
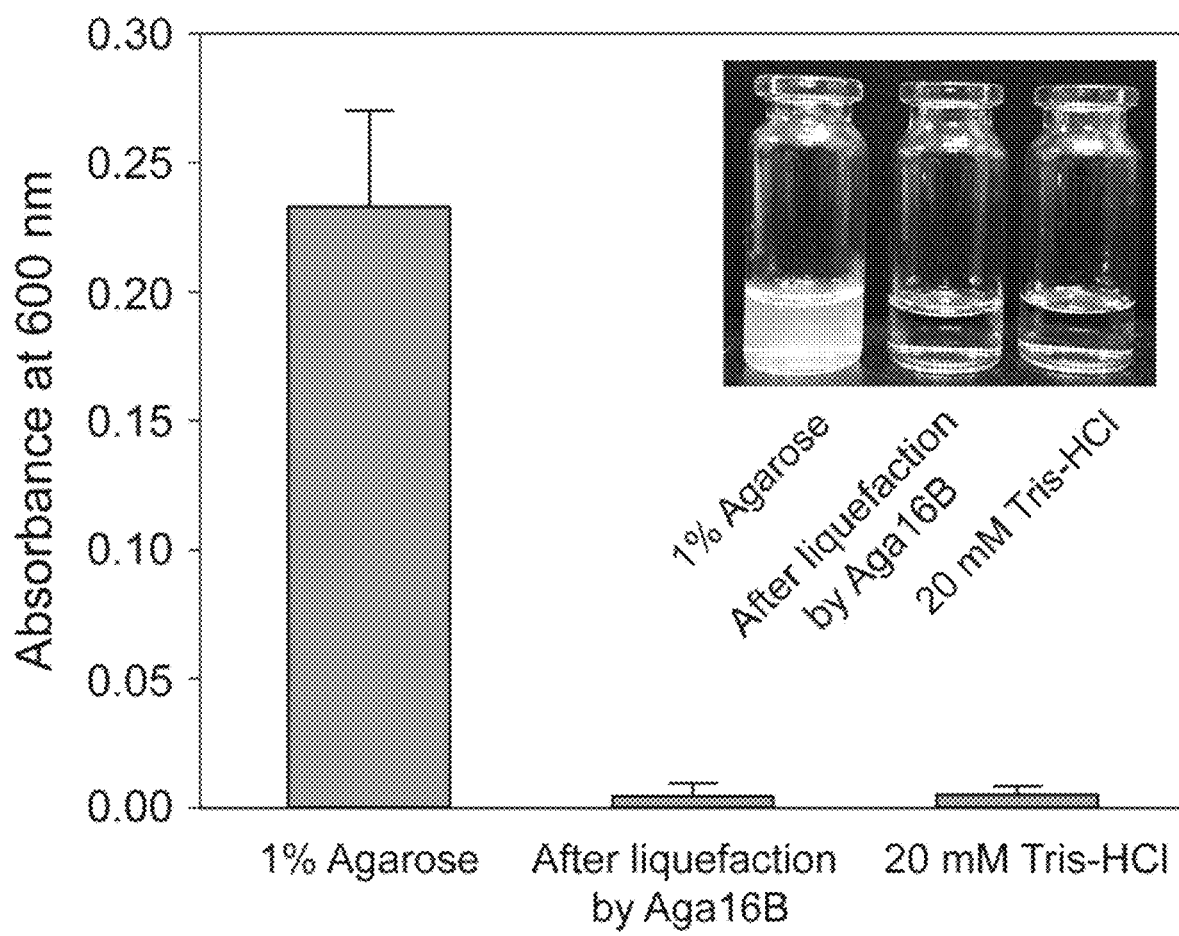
FIG. 8 is a result which observes the degree to which agarose is liquefied by Aga16B.

As illustrated in FIG. 8, the 1% agarose was gelled, became opaque, and produced a high absorbance at 600 nm, and the Aga16B reaction product showed an absorbance at the same level as that of the 20 mM Tris-HCl. Through this, it was confirmed that Aga16B was obtained by enzymatically liquefying agarose.

<Example 10> Production of 3,6-Anhydro-L-Galactose Using Aga16B, Aga50D, and NABH In order to produce a monosaccharide by applying Aga16B to an enzymatic process, D-galactose and 3,6-anhydro-L-galactose were produced by using Aga16B, Aga50D and NABH enzymes.

For this purpose, after 5% agarose was produced in 200 mL of a 20 mM Tris-HCl buffer (pH 7.0) and dissolved using an autoclave at 120° C. for 10 minutes, 19.7 mg of Aga16B was added thereto in order to break down agarose, the resulting mixture was allowed to react at 200 rpm for 12 hours at 55° C., and DP4 and DP6 were produced as the reaction products.

In order to break down these reaction products, these reaction products were allowed to react with an exo-type disaccharide-producing enzyme, Aga50D (20 mg), at 25° C. and 200 rpm, and neoagarobiose was produced as a reaction product.

After this reaction, SdNABH (10 mg) was allowed to react in order to produce D-galactose and 3,6-anhydro-L-galactose.

Aga50D and SdNABH were prepared as described in Korean Patent Application Laid-Open No. 2010-0040438 (Apr. 20, 2010) and Korean Patent Application Laid-Open No. 2013-0085017 (Jul. 26, 2013), respectively, and used.

Figure 9A:
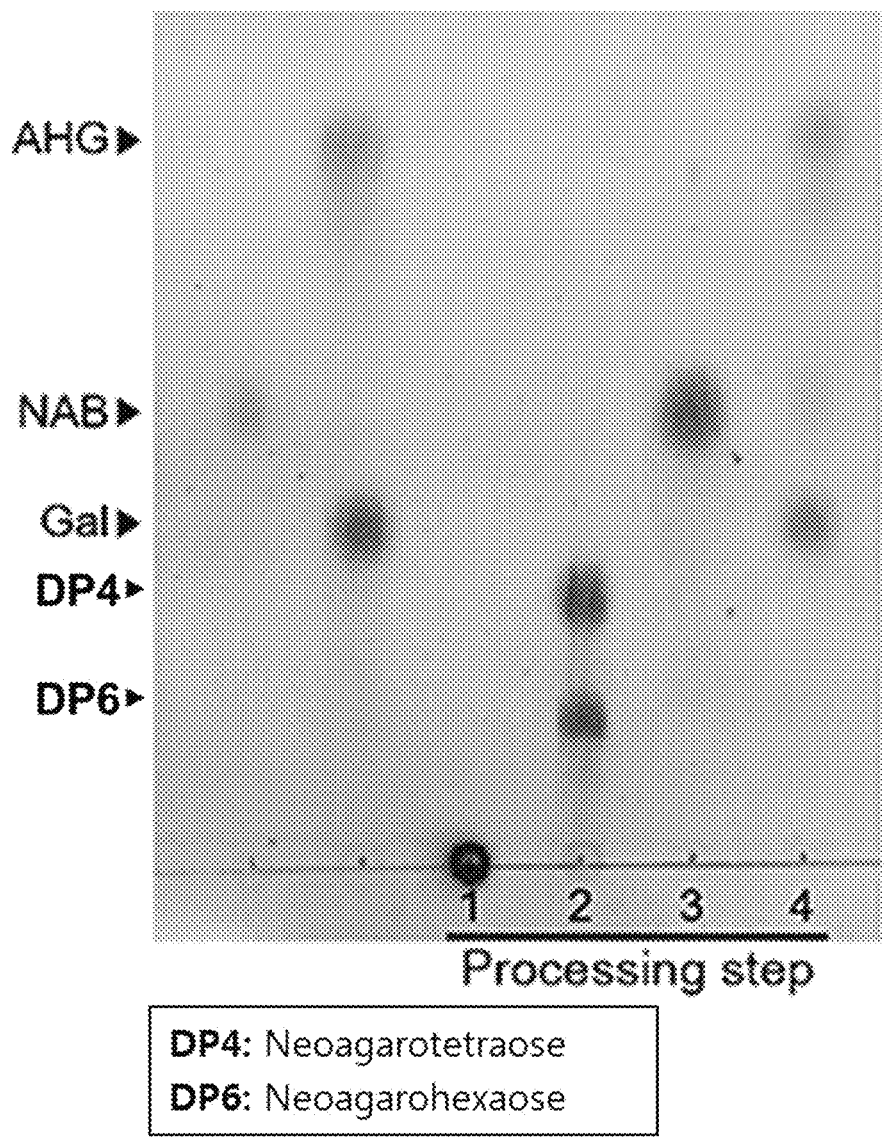
FIG. 9a is a TLC analysis result illustrating the enzymatic saccharification of agarose by Aga16B, Aga50D, and NABH, Processing step No. 1 is a 5% agarose substrate, Processing step No. 2 is a reaction product after a reaction of agarose with Aga16B, Processing step No. 3 is a reaction product of Aga15D with respect to Aga16B reaction products, and Processing step No. 4 is a reaction product of NABH with respect to Aga15D reaction products.
Figure 9B:
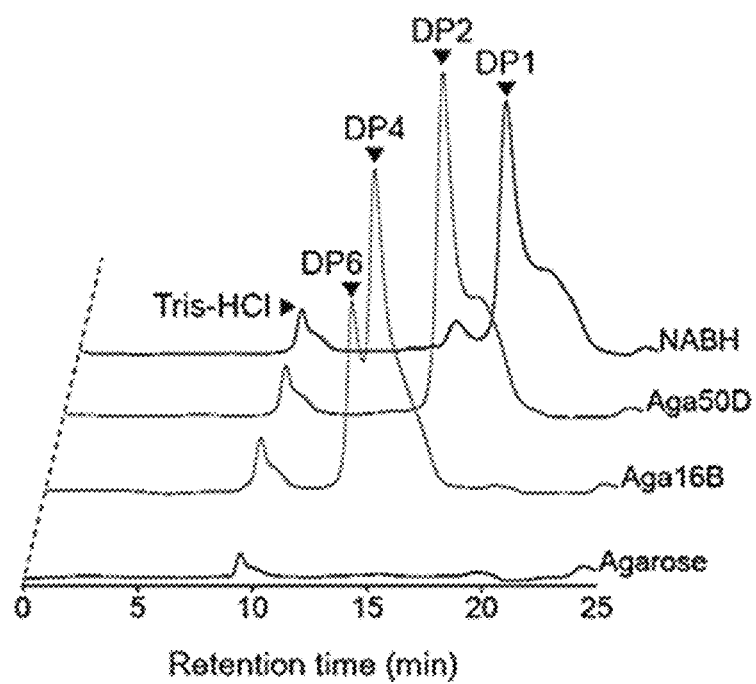
FIG. 9b is an HPLC analysis result illustrating the enzymatic saccharification of agarose by Aga16B, Aga50D, and NABH.

The pattern of each reaction product was confirmed through HPLC analysis (FIG. 9).

<Example 11> Quantitative Analysis of 3,6-Anhydro-L-Galactose Through GC-MS Analysis The reaction product of SdNABH produced through Example 10 was analyzed by GC/MS and quantified. For this purpose, a derivatization process for the GC/MS analysis was performed. 20 µL of the reaction product was dried with a Speed-Vac, and then 10 μl of O-methylhydroxylamine hydrochloride in pyridine at a concentration of 4% (w/v) was added thereto, the resulting mixture was allowed to react at 30° C. for 90 minutes, 45 μL of N-methyl-N-(trimethylsilyl) trifluoroacetamide was added thereto, and an analysis sample was prepared by allowing the resulting mixture to react at 37° C. for 30 minutes. For the instrument conditions for the GC/MS analysis, by using a DB5-MS capillary column, the column temperature was maintained at 100° C. for 3.5 minutes, and after the temperature was increased to 160° C., the temperature was maintained for 20 minutes. After the temperature was increased to 200° C., the temperature was maintained for 15 minutes, and finally, after the temperature was increased to 280° C., the temperature was maintained for 5 minutes. After 0.5 μL of the sample was loaded, the sample was analyzed at 5 split ratios.

As illustrated in Table 3, as a result of measuring the monosaccharide yield on the basis of the GC/MS quantitative result, a yield of 0.81 g/g agarose was obtained, which is a value corresponding to 72.5% of the maximum yield which may be theoretically obtained.

TABLE 3

Production Yield of 3,6-Anhydro-L-Galactose Produced through Enzymatic Saccharification

| Agarose saccharification method | Enzymatic saccharification method using acetic acid pretreatment and Aga50D, ABG, and NABH (CH Lee et al., (2015) Process Biochem 50: 1629-1633) | Enzymatic saccharification method using Tris-HCl buffer pretreatment and Aga50D, ABG, and NABH (CH Lee et al., (2015) Process Biochem 50: 1629-1633) | Enzymatic saccharification method using Aga16B, Aga50D, and NABH |
|---|---|---|---|
| Saccharification yield (% of theoretical maximum) | 50.5 | 44.9 | 72.5 |

The present invention may be applied to the field in which monosaccharides are produced from red algae.

What is claimed is:

1. A method for producing galactose or 3,6-anhydro-L-galactose, comprising reacting an agarase comprising the amino acid sequence of SEQ ID NO: 1 with not-pretreated agarose or agar as a substrate under a temperature range of 50 to 60° C. to produce neoagarotetraose or neoagarohexaose as a reaction product, reacting an agarase comprising the amino acid sequence of SEQ ID NO: 3 with the reaction product to produce neoagarobiose, and reacting an α-neoagarobiose hydrolase comprising the amino acid sequence of SEQ ID NO: 4 with neoagarobiose to produce galactose or 3,6-anhydro-L-galactose.

2. The method of claim 1, wherein the reaction of the agarase with agarose or agar is performed within a temperature range of 55° C., under a condition of 0 to 300 rpm, and at a pH of 5 to 9 for 30 minutes to 7 days.

3. The method of claim 1, wherein the reaction by the agarase and or the α-neoagarobiose hydrolase is performed within a temperature range of 20 to 40° C. and under a condition of 0 to 200 rpm for 30 minutes to 7 days.

* * * * *